(12) United States Patent
Ramoser et al.

(10) Patent No.: US 8,064,680 B2
(45) Date of Patent: Nov. 22, 2011

(54) PROCESS FOR SEGMENTING LEUKOCYTES

(75) Inventors: Herbert Ramoser, Vienna (AT); Rupert Ecker, Strasshof A.D. Nordbahn (AT)

(73) Assignee: Tissue Gnostics GmbH, Vienna (AT)

( * ) Notice: Subject to any disclaimer, the term of this patent is extended or adjusted under 35 U.S.C. 154(b) by 912 days.

(21) Appl. No.: 11/957,715

(22) Filed: Dec. 17, 2007

(65) Prior Publication Data
US 2008/0212868 A1 Sep. 4, 2008

Related U.S. Application Data

(63) Continuation of application No. PCT/AT2006/000244, filed on Jun. 14, 2006.

(30) Foreign Application Priority Data

Jun. 15, 2005 (AT) ................................. A 1010/2005

(51) Int. Cl.
*G06K 9/00* (2006.01)
*C07H 21/04* (2006.01)
(52) U.S. Cl. ......................... 382/134; 382/164; 536/23.1
(58) Field of Classification Search .................. 382/103, 382/128, 129, 130, 131, 132, 133, 134, 162, 382/164, 168, 173, 181, 194, 199, 203, 219, 382/232, 254, 276, 291, 305, 312; 435/6, 435/34; 536/23.1
See application file for complete search history.

(56) References Cited

U.S. PATENT DOCUMENTS

| | | | |
|---|---|---|---|
| 6,221,607 B1 * | 4/2001 | Tsipouras et al. ................ 435/6 |
| 7,048,929 B1 * | 5/2006 | Sodroski et al. ........... 424/188.1 |
| 7,049,074 B2 * | 5/2006 | Schwartz .......................... 435/6 |
| 7,323,318 B2 * | 1/2008 | Fan et al. ......................... 435/29 |
| 7,657,076 B2 * | 2/2010 | Vaisberg et al. .............. 382/133 |
| 7,817,840 B2 * | 10/2010 | Mattheakis et al. .......... 382/133 |

OTHER PUBLICATIONS

Ramoser et al.: "Leukocyte segmentation and classification in blood-smear images", Proceedings of the 2005 IEEE Engineering in Medicine and Biology 27th Annual Conference, Shanghai, China, pp. 3371-3374, Sep. 1-4, 2005.

(Continued)

*Primary Examiner* — Seyed Azarian
(74) *Attorney, Agent, or Firm* — Laurence A. Greenberg; Werner H. Stemer; Ralph E. Locher

(57) ABSTRACT

A method for segmenting stained leukocytes in blood smears includes the following steps: the pixels of the digital images taken of the blood smears are allocated to one of at least three pixel classes according to their chromaticity values; the chromaticity values of all pixels of the image are subjected to the same transformation with which the pixels allocated to the class of the image background appear at least almost white; a transformation of the stained image obtained takes place into an alternative color space, which represents the hue, color saturation and color intensity separately, and hue, color saturation and color intensity of all pixels are ascertained; a probability value is calculated for each pixel for its association to a leukocyte, the probability value corresponding to the product of the probability value for the hue of the leukocyte nucleus with at least one further probability value; then these probability values are defined with reference to previously ascertained and defined associations, and the pixels with a high value of the product of the probability values are considered as belonging to a leukocyte.

15 Claims, 3 Drawing Sheets

OTHER PUBLICATIONS

Figure 1:
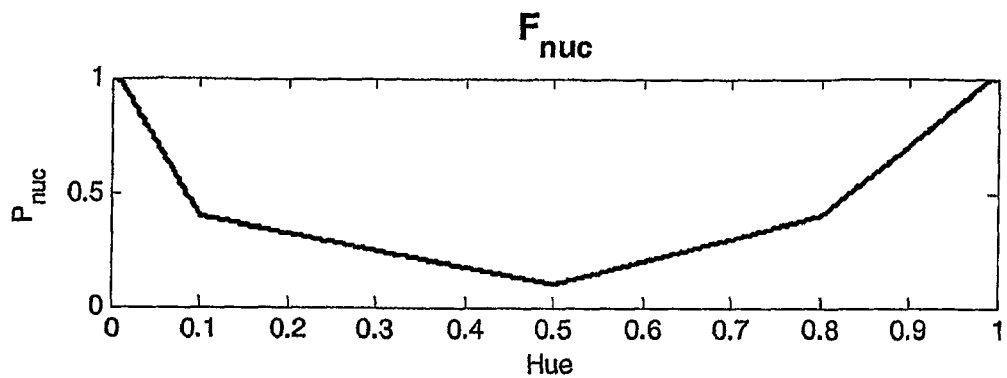
Figure 2:
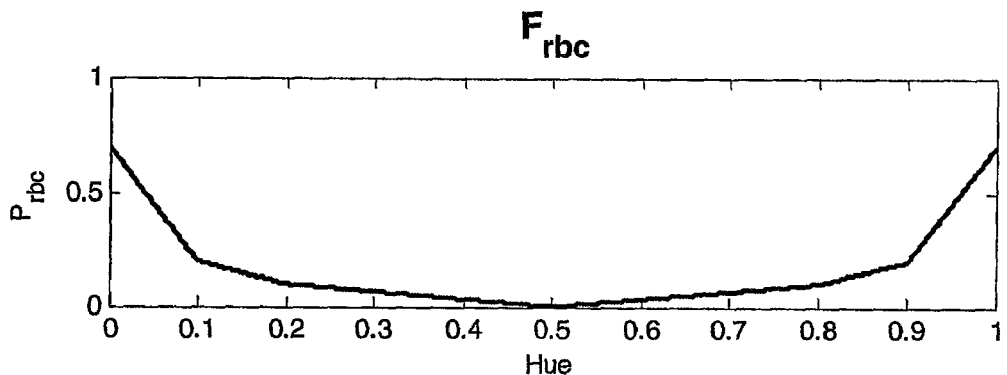
Figure 3:
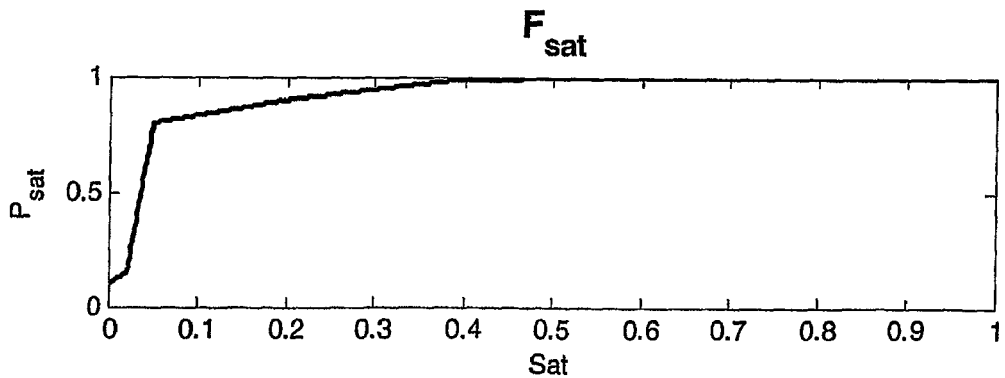

Montseny et al.: "A Fuzzy Approach to White Blood Cells Segmentation in Color Bone Marrow Images", Fuzzy Systems, 2004 IEEE International Conference in Budapest, Hungary, Jul. 25-29, 2004, Piscataway, NJ, USA, IEEE, vol. 1, pp. 173-178.

Sinha et al.: "Automation of Differential Blood Count", IEEE Tencon 2003, Conference of Convergent Technologies for the Asia-Pacific Region. Bangalore, India, Oct. 15-17, 2003, IEEE Region 10th Annual Conference, New York, NY, vol. 4, pp. 547-551.

* cited by examiner

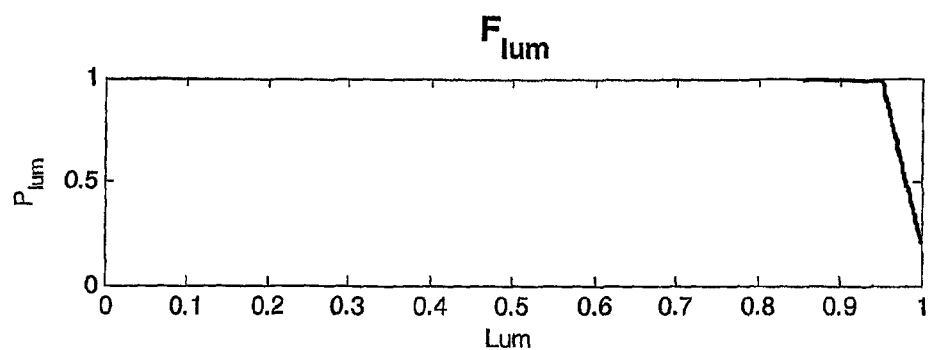
Fig. 4
Fig. 5
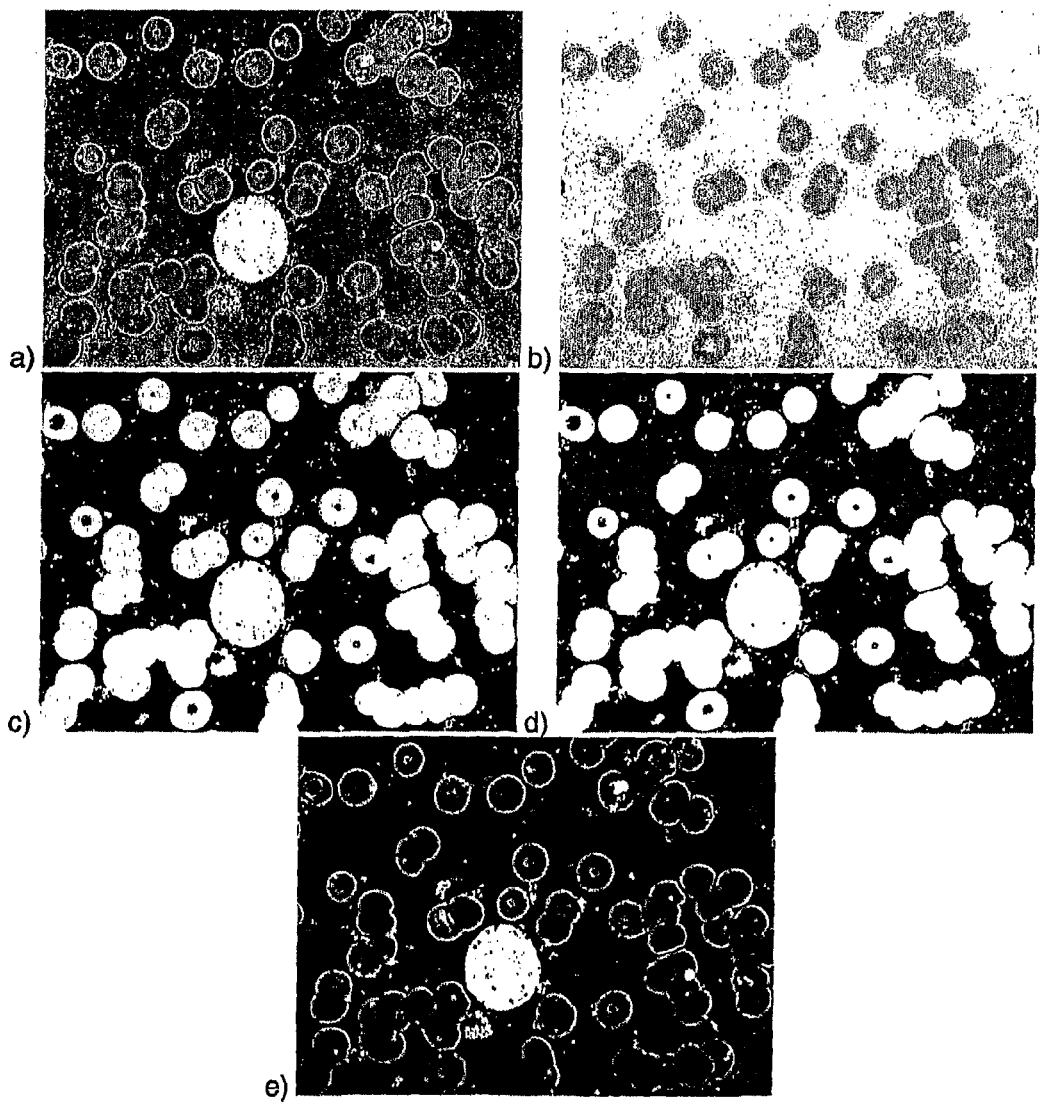

PROCESS FOR SEGMENTING LEUKOCYTES

CROSS-REFERENCE TO RELATED APPLICATION

This is a continuation, under 35 U.S.C. §120, of copending international application PCT/AT2006/000244, filed Jun. 14, 2006, which designated the United States; this application also claims the priority, under 35 U.S.C. §119, of Austrian patent application A 1010/2005, filed Jun. 15, 2005; the prior applications are herewith incorporated by reference in their entirety.

BACKGROUND OF THE INVENTION

Field of the Invention

The invention relates to a process for segmenting stained leukocytes in blood smears.

SUMMARY OF THE INVENTION

It is a primary object of the invention to provide a process for the segmentation of leukocytes that improves the heretofore-known devices and methods of the general type and which provides for the quickest and most accurate segmenting and, if necessary, subsequent classification of leukocytes with reference to images which were taken of stained blood smears. The evaluation should reproduce the form and location of the leukocytes as well as the nucleus of the leukocytes as true to life as possible without great calculating expenditure, so that a possible subsequent classification of the leukocytes is quickly possible and without a large expenditure.

With the foregoing and other objects in view there is provided, in accordance with the invention, a method for segmenting stained leukocytes in a blood smear, which comprises:

defining at least three pixel classes, including erythrocytes, leukocytes (including cell nucleii and cytoplasms), and image background;

allocating pixels of a digital image taken of the blood smear to one of the at least three pixel classes in accordance with a chromaticity value (e.g., RGB) thereof;

subjecting the chromaticity values of all pixels of the image to a common transformation, upon which the pixels allocated to the class of image background appear substantially white;

transforming the color image to an alternative color space representing a hue, a color saturation, and a color intensity separately, and ascertaining the hue, the color saturation, and the color intensity of all pixels;

calculating a probability value for each pixel for an association thereof to a leukocyte, the probability value corresponding to a product of a probability value for the hue of the leukocyte nucleus with at least one further probability value, and selecting the at least one further probability value from the group of probability values consisting of a probability value for a non-association of a pixel to an erythrocyte hue, or a probability value allocated to a color saturation value of each pixel, or a probability value allocated to a color intensity value or the luminosity of each pixel;

defining the probability values with reference to previously ascertained and defined associations; and considering pixels with a high value for the product of the probability value as representing a leukocyte.

Preferably, the common transformation comprises dividing the chromaticity values of the individual pixels by the average chromaticity value ascertained for the pixels of the background.

It was shown that a decidedly accurate image of the leukocytes contained in the blood smear could be obtained with little calculating expenditure by the transformation undertaken and the subsequent probability determinations and evaluation in view of probability products.

In accordance with an added feature of the invention, the leukocyte pixels or the separation of the background are accented by applying a threshold value method to the probability products obtained for the pixels or to the resultant probability image, whereby a quality measurement $Q(R)$ is calculated for each segmented region to define the threshold. Preferably, there is formed a ratio of a number of leukocyte nucleus pixels within a segmented region to a total number of pixels in the known region, and the threshold value of the best quality measurement thus obtained is used. This improves the contrast of the leukocytes in the observed image.

In accordance with an additional feature of the invention, the a leukocyte is further segmented while taking into account the luminosity, saturation, and hue values of the respective pixel, standardizing the values between preset limits and grouping the values using a clustering. In a preferred embodiment, we use k-means clustering.

Clustering leads to a simplification of the calculations of the evaluation process. Clustering refers to a compilation of image points having optional or specific similar properties. The term "k-means clustering" refers to an algorithm in which a desired number k of clusters and a function for determining the center of a cluster is known. The algorithm proceeds as follows:

a) Initialization: (incidental) selection of k cluster centers
  b) Allocation: Each object is allocated to the cluster center closest to it
  c) Recalculation: The cluster centers are recalculated for each cluster
  d) Repetition: If the allocation of the objects now changes, continue with step b, otherwise stop Data is clustered in a preset number of groups based on preset starting points.

In accordance with another feature of the invention, the method comprises determining form features and form parameters of the segmented leukocytes and allocating the segmented leukocytes to the different leukocyte types in dependence on the form features and form parameters.

In accordance with a concomitant feature of the invention, the probability values used for calculating the probability value of the pixels are determined via heuristic image functions. The image functions may be configured partially with linear sections.

The heuristic image functions were determined with reference to test image series or calibrations.

With the above objects in view there is also provided a computer program product having programming code stored on a computer-readable data carrier and configured, when executed on a computer, to carry out the above-outlined method.

Other features which are considered as characteristic for the invention are set forth in the appended claims.

Although the invention is illustrated and described herein as embodied in process for segmenting leukocytes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF DRAWING

Figure 7:
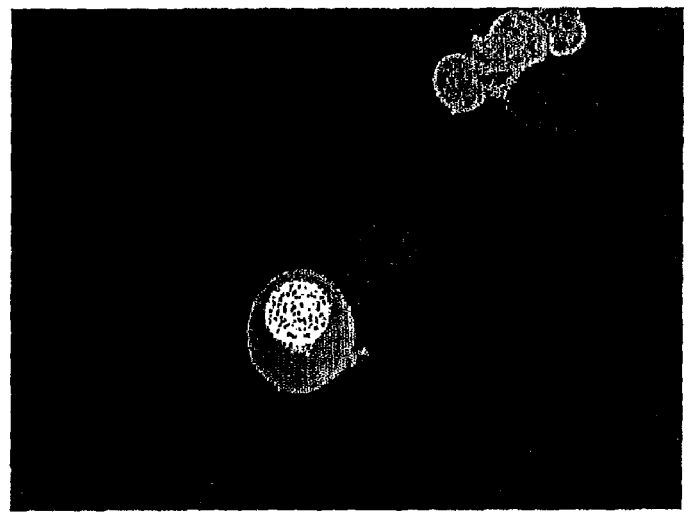

FIGS. 1, 2, 3, 4, and 6 are graphs showing various optical functions or probability curves;

FIG. 5, with subparts A, B, C, D, and E, shows various probability images which are obtained in the course of carrying out the process according to the invention; and FIG. 7 shows a segmented leukocyte.

DETAILED DESCRIPTION OF THE INVENTION

The invention will be described by way of example in the following with reference to the segmenting of leukocytes in images of stained blood smears. It is quite possible to also evaluate images of leukocytes obtained in another manner.

Images of stained blood smears are obtained by taking these images with a color camera which is mounted on the tube of a fluoroscopic microscope.

The leukocytes are present in a stained form. The coloring of the leukocyte nucleus is significantly contrasted compared with the coloring of the cytoplasm, in particular darker.

The saturation (Sat(R,G,B)) and the luminosity (Lum(R,G,B)) of a pixel are referred to as features for the characterization of the nucleus pixel and the background pixel. The calculation of the saturation and luminosity of a pixel from the RGB color components is shown in the following.

$$RGBmax = max(R, G, B)$$

$$RGBmin = min(R, G, B)$$

$$Sat(R, G, B) = \begin{cases} 0, & \text{if } RBGmax(R, G, B) = 0 \\ \dfrac{RGBmax(R, G, B) - RGBmin(R, G, B)}{RGBmax(R, G, B)}, & \text{otherwise} \end{cases}$$

$$Lum(R, G, B) = \frac{RGBmax(R, G, B) + RGBmin(R, G, B)}{2}$$

Three pixel classes are defined: erythrocytes (red blood cells), leukocytes or leukocyte nucleii (white blood corpuscles) and image background, whereby it is assumed that the background region forms the largest number of pixels in an image, followed by the erythrocytes and the leukocytes. Every pixel is allocated to one of these three classes with the method "k-means clustering". If more than 90% of all pixels are in the class background, the allocation process is repeated to avoid an error segmenting. The procedure in "k-means clustering" is known from C. M. Bishop, *Neural Networks for Pattern Recognition*; Oxford University Press, Oxford, England, 1995.

The background color of an image of a blood smear appears in the stained images taken, e.g. with non-ideal lighting, non-optimal white balancing of the color camera or through the glass of the object slide does not appear ideally white. If a multiplicative color mixture is accepted, then the color for each new pixel $C' \in \{R,G,B\}$ can be transformed for each pixel $C \in \{R,G,B\}$ in the image with the operations described in the following in such a way that every background pixel appears almost white.

$$C' = \begin{cases} 255 \cdot \min\left(\dfrac{C}{\overline{C}_{bg}}\right) & \text{if } \overline{C}_{bg} > 0 \text{ and } \min\left(\dfrac{C}{\overline{C}_{bg}}\right) \leq 1 \\ 255 & \text{if } \overline{C}_{bg} > 0 \text{ and } \min\left(\dfrac{C}{\overline{C}_{bg}}\right) > 1 \end{cases}$$

$\overline{C}_{bg} \in \{R,G,B\}$ is the average color of the image background. In $\overline{C}_{bg} = 0$, there is a black image on the assumption of a multiplicative color mixture.

In the course of an image transformation of the RGB color zone into an alternative color zone, the hue is determined in addition to saturation and luminosity. The hue (Hue(R,G,B)) of each pixel is transformed as follows in a circle which is subdivided into six sectors:

$$C_n = \frac{RGBmax(R, G, B) - C'}{RGBmax(R, G, B) - RGBmin(R, G, B)},$$

$$C' \in \{R, G, B\}, C_n \in \{R_n, G_n, B_n\}$$

New pixel values $C_n(R_n, G_n, B_n)$ are calculated from the pixel values C'(RGB). (R . . . red channel, G . . . green channel, B . . . blue channel)

if R=RGBmax(R,G,B)

$$Hue(R, G, B) = \begin{cases} 5 + B_n & \text{if } G = RGBmin(R, G, B) \\ 1 - G_n & \text{otherwise} \end{cases}$$

else if G=RGBmax(R,G,B)

$$Hue(R, G, B) = \begin{cases} 1 + R_n & \text{if } B = RGBmin(R, G, B) \\ 3 - B_n & \text{otherwise} \end{cases}$$

else $$Hue(R, G, B) = \begin{cases} 3 + G_n & \text{if } R = RGBmin(R, G, B) \\ 5 - R_n & \text{otherwise} \end{cases}$$

end if (end of the "end if" loop and the next step follows)

$$Hue(R, G, B) = \frac{Hue(R, G, B)}{6}$$

The leukocyte probability is calculated for each pixel via the product of the probability value for the nucleus hue and at least one further probability value, namely the probability value for the "non-erythrocyte hue" and/or for the saturation and/or luminosity. The individual probability values are determined via heuristic image functions determined with reference to test image series. The image functions ascertained accordingly are graphically illustrated in FIGS. 1, 2, 3 and 4. The piece by piece preset linear sections of the image functions enable an efficient interpolation or the application of reference tables in the course of evaluation images. To increase the evaluation accuracy, the product of all probability values can be determined. Generally, the probability product of the nucleus hue Pnuc with a further probability value suffices.

The combined leukocyte probability is then calculated for each pixel as follows:

$$P_{wbc}(R,G,B) = P_{nuc}(\text{Hue}(R,G,B))P_{rbc}(\text{Hue}(R,G,B))P_{sat}(\text{Sat}(R,G,B))P_{lum}(\text{Lum}(R,G,B))$$

With reference to a sample image, FIG. 5 (parts A, B, C, D, E) shows the individual probability images or the combined probability image. Part A of FIG. 5 shows a probability image for the nucleus hue, part B shows a probability image for the "non-erythrocyte hue", part C shows a probability image for the saturation, part D shows a probability image for the luminosity, and part E of FIG. 5 shows the probability image obtained for a leukocyte. Light pixels correspond with high probability values, dark pixels with low probability values.

The improve the image quality, the method Maximally Stable Extremal Regions can be applied to the probability image according to part E of FIG. 5.

An MSER method is outlined in Matas, Chum, Urban, and Pajdla: *Robust Wide Baseline Stereo From Maximally Stable Extremal Regions*; in the International Journal of Computer Vision; Vol. 22; No. 10; pp. 761-767; 2004; or in Matas, Chum, Urban, and Pajdla; *Distinguished Regions for Wide-Baseline Stereo*; Report CTU-CMP-2001-33; Prague, Czech Republic: Center for Machine Perception, Czech Technical University, 2001.

In the course of an MSER method, an image is converted over and over again into different binary images, i.e. every time with another threshold value which continuously assumes another value, e.g. between 1 to 254.

The light leukocyte nucleus and the cytoplasm of the leukocyte exhibiting a somewhat lower luminosity can be clearly seen in FIG. 5e.

The quality constant Q(R) is subsequently calculated for each segmented region R', i.e. for images having associated image points with similar properties, referring to nucleus pixels:

```
if number of nucleus pixels in R<T_nucleus
    Q(R) = 0        T_nucleus = predetermined threshold value
else
    morphological opening of R
    fill holes in R
    select largest region of R
    Q(R) = Compactness(R)NucleusRatio(R)
end
```

The term morphological opening refers to a combination of the operators erosion with subsequent dilatation. In the binary image (each image point has either the value "0" or "1"), the erosion operator causes the reduction of all surfaces with the value "1" about an edge of the width of an image point. An image point having the value "0" retains its value, while the image point with the value "1" only retains its value if all adjacent image points also have the value "1". In the binary image, the dilatation operator causes the enlargement of all surfaces having the value "1" about an edge of the width of an image point. The operation "fill holes" is applied to a binary image (each image point has either the value "0" or "1"). If a surface of image points having the value "0" is surrounded by a surface of image points having the value "1", then these image points with the value "0" are replaced by image points with the value "1".

The compactness of a segmented image region R is calculated as follows:

$$\text{Compactness}(R) = \frac{2\sqrt{\pi \text{Area}(R)}}{\text{Perimeter}(R)}$$

Figure 6:
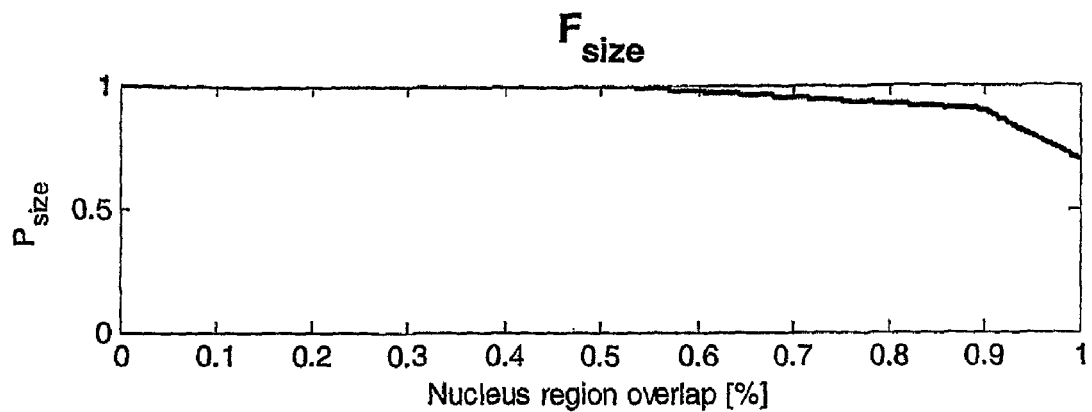

The ratio of the number of nucleus pixels NucleusArea(R) of the image region R to the total pixel number of the image region R Area(R) gives a probability ratio for the nucleus surface per total area of the image region R as per FIG. 6.

$$\text{NucleusRatio}(R) = F_{size}\left[\frac{\text{NucleusArea}(R)}{\text{Area}(R)}\right]$$

$F_{size}(x)$ is the corresponding image function. The pattern of $F_{size}(x)$ is illustrated in FIG. 6.

The quality Q(R) of the regions ascertained with the MSER method is stored in a tree structure. To segment leukocytes, the region with the highest Q(R) is selected for each limb of the tree. If a limb has several branches whose average value of Q(R) is higher, then the branches are selected as segmenting. FIG. 7 shows those Maximally Stable Extremal Regions (image regions) which contain cell nucleus pixels. The luminosity is proportional to the number of those following, i.e. to the number of branches of a limb.

After the leukocytes were segmented in this way in the images, the leukocytes can be accurately classified.

This classification may comprise a segmentation of cytoplasms and cell nucleus, followed by a recordation of the texture and form features and a comparison of the recorded properties with preset comparative values. In dependency on the comparison that has taken place, the segmented leukocytes are then allocated to the various types of leukocytes.

The invention claimed is:

1. A method for segmenting stained leukocytes in a blood smear, which comprises:
    defining at least three pixel classes, including erythrocytes, leukocytes, and image background;
    allocating pixels of a digital image taken of the blood smear to one of the at least three pixel classes in accordance with a chromaticity value thereof;
    subjecting the chromaticity values of all pixels of the image to a common transformation, upon which the pixels allocated to the class of image background appear substantially white;
    transforming the color image to an alternative color space representing a hue, a color saturation, and a color intensity separately, and ascertaining the hue, the color saturation, and the color intensity of all pixels;
    calculating a probability value for each pixel for an association thereof to a leukocyte, the probablity value corresponding to a product of a probability value for the hue of the leukocyte nucleus with at least one further probability value, and selecting the at least one further probability value from the group of probability values consisting of a probability value for a non-association of a pixel to an erythrocyte hue, or a probability value allocated to a color saturation value of each pixel, or a probability value allocated to a color intensity value or the luminosity of each pixel;
    defining the probability values with reference to previously ascertained and defined associations; and considering pixels with a high value for the product of the probability value as representing a leukocyte.

2. The method according to claim 1, wherein the allocating step comprises clustering the pixels.

3. The method according to claim 1, wherein the allocating step comprises subjecting the pixels to k-means clustering.

4. The method according to claim 1, wherein the chromaticity values are RGB chromaticity values.

5. The method according to claim 1, wherein the leukocytes are defined to include cell nucleii and cytoplasms.

6. The method according to claim 1, wherein the common transformation comprises dividing the chromaticity values of the individual pixels by the average chromaticity value ascertained for the pixels of the background.

7. The method according to claim 1, which comprises accentuating the leukocyte pixels or the separation of the background by applying a threshold value method to the probability products obtained for the pixels or to the resultant probability image, whereby a quality measurement Q(R) is calculated for each segmented region to define the threshold.

8. The method according to claim 7, which comprises forming a ratio of a number of leukocyte nucleus pixels within a segmented region to a total number of pixels in the known region, and using the threshold value of the best quality measurement thus obtained.

9. The method according to claim 1, which comprises further segmenting a leukocyte while taking into account the luminosity, saturation, and hue values of the respective pixel, standardizing the values between preset limits and grouping the values using a clustering.

10. The method according to claim 9, which comprises using a k-means clustering.

11. The method according to claim 1, which comprises determining form features and form parameters of the segmented leukocytes and allocating the segmented leukocytes to the different leukocyte types in dependence on the form features and form parameters.

12. The method according to claim 1, which comprises determining the probability values used for calculating the probability value of the pixels via heuristic image functions.

13. The method according to claim 12, wherein the heuristic image functions were determined with reference to test image series or calibrations.

14. The method according to claim 12, wherein the image functions are configured partially with linear sections.

15. A computer program product, comprising a computer-readable medium having programming code stored thereon in non-transitory form, the programming code being configured, when loaded into and executed on a computer, to carry out the method according to claim 1.

* * * * *